(12) United States Patent
Sato et al.

(10) Patent No.: US 11,193,099 B2
(45) Date of Patent: Dec. 7, 2021

(54) TEMPERATURE ADJUSTMENT APPARATUS

(71) Applicant: HITACHI HIGH-TECHNOLOGIES CORPORATION, Tokyo (JP)

(72) Inventors: Wataru Sato, Tokyo (JP); Nobuyuki Isoshima, Tokyo (JP); Kohshi Maeda, Tokyo (JP); Daisuke Morishima, Tokyo (JP)

(73) Assignee: HITACHI HIGH-TECH CORPORATION, Tokyo (JP)

( * ) Notice: Subject to any disclaimer, the term of this patent is extended or adjusted under 35 U.S.C. 154(b) by 218 days.

(21) Appl. No.: 15/758,509

(22) PCT Filed: Jul. 27, 2016

(86) PCT No.: PCT/JP2016/071950
§ 371 (c)(1),
(2) Date: Mar. 8, 2018

(87) PCT Pub. No.: WO2017/043203
PCT Pub. Date: Mar. 16, 2017

(65) Prior Publication Data
US 2018/0245031 A1    Aug. 30, 2018

(30) Foreign Application Priority Data

Sep. 9, 2015   (JP) .............................. JP2015-177137

(51) Int. Cl.
*C12M 1/38* (2006.01)
*C12M 1/00* (2006.01)
(Continued)

(52) U.S. Cl.
CPC ................. *C12M 1/38* (2013.01); *B01L 7/52* (2013.01); *C12M 1/00* (2013.01); *C12M 41/12* (2013.01);
(Continued)

(58) Field of Classification Search
CPC ....................................................... B01L 7/52
See application file for complete search history.

(56) References Cited

U.S. PATENT DOCUMENTS

| | | | |
|---|---|---|---|
| 2002/0072112 A1* | 6/2002 | Atwood | B01L 3/50851 |
| | | | 435/303.1 |
| 2005/0056635 A1 | 3/2005 | Suzuki et al. | |

(Continued)

FOREIGN PATENT DOCUMENTS

| | | |
|---|---|---|
| JP | 07-190822 A | 7/1995 |
| JP | 08-148725 A | 6/1996 |

(Continued)

OTHER PUBLICATIONS

English machine translation of Document No. JP 2004125182 provided by Espacenet (Year: 2004).*

(Continued)

*Primary Examiner* — Holly Kipouros
(74) *Attorney, Agent, or Firm* — Miles & Stockbridge, P.C.

(57) ABSTRACT

Provided is a highly reliable temperature adjustment apparatus which uses a temperature adjustment element and quantitatively evaluates the temperature adjustment performance of the temperature adjustment element. The temperature adjustment apparatus is provided with: a temperature adjustment element; one or more temperature detection elements provided near the temperature adjustment element; a calculation unit for calculating the output of the temperature detection element; and a display unit for displaying at least one of a time calculated by the calculation unit as a time at which the temperature adjustment performance of the temperature adjustment is predicted to be below a desired level, the number of operations and the time of current conduction or a warning based on the result of calculation.

6 Claims, 6 Drawing Sheets

(51) Int. Cl.
*B01L 7/00* (2006.01)
*C12M 1/34* (2006.01)
*C12M 1/36* (2006.01)
*B01L 3/00* (2006.01)
*F25B 21/04* (2006.01)

(52) U.S. Cl.
CPC ............ *C12M 41/48* (2013.01); *B01L 3/5082* (2013.01); *B01L 2200/147* (2013.01); *B01L 2300/1822* (2013.01); *F25B 21/04* (2013.01); *F25B 2500/19* (2013.01)

(56) References Cited

U.S. PATENT DOCUMENTS

| 2014/0286372 | A1 | 9/2014 | Kobayashi et al. |
| 2015/0367348 | A1 | 12/2015 | Sano et al. |
| 2018/0015476 | A1* | 1/2018 | Maeda ................ C12Q 1/6844 |

FOREIGN PATENT DOCUMENTS

| JP | 2001-521379 A | 11/2001 |
| JP | 2002-333417 A | 11/2002 |
| JP | 2004-125182 A | 4/2004 |
| JP | 2004-309073 A | 11/2004 |
| JP | 2004-319953 A | 11/2004 |
| JP | 2006-165200 A | 6/2006 |
| JP | 2008-232503 A | 10/2008 |
| JP | 2010-104382 A | 3/2010 |
| JP | 2014-143927 A | 8/2014 |
| JP | 2014-182694 A | 9/2014 |
| JP | 2016-144431 A | 8/2016 |
| WO | WO 98/43740 A2 | 10/1998 |
| WO | WO 2006/054690 A1 | 5/2006 |
| WO | WO 2015/190249 A1 | 12/2015 |

OTHER PUBLICATIONS

Lienig et al., Fundamentals of Electronic Systems Design, 2017, Springer, pp. 113-114 (Year: 2017).*
International Search Report from International Patent Application No. PCT/JP2016/071950, dated Sep. 20, 2016.
Written Opinion of the International Searching Authority from PCT/JP2016/071950, dated Sep. 20, 2016.
International Preliminary Reporton Patentability from International Patent Application No. PCT/JP2016/071950, submitted Sep. 11, 2017.

* cited by examiner

TEMPERATURE ADJUSTMENT APPARATUS

TECHNICAL FIELD

The present invention relates to a temperature adjustment apparatus that uses a temperature adjustment element.

BACKGROUND ART

In a temperature adjustment apparatus, a ceramic heater or a film heater is used as a temperature adjustment element for adjusting an increase in temperature by heating, and a Peltier element, a cooling fan, or a cooling water chiller unit is used as a temperature adjustment element for adjusting a decrease in temperature by cooling. In particular, because a Peltier element can be used for both heating and cooling, it has been widely used as a temperature adjustment element. This Peltier element has a characteristic that the one side of this element absorbs heat to decrease temperature and the other side radiates heat to increase temperature by impressing current through the element. By increasing the amount of the impressed current, it becomes possible to increase the amount of heat absorbed or radiated by the element, and in addition, by inverting the direction of the impressed current, it becomes possible to invert the heat-absorbing characteristic of the one side and the heat-radiating characteristic of the other side, therefore the Peltier element can be used for both heating and cooling and has been widely used for accurate temperature control. However, if excessively successive heating/cooling cycles are applied to a Peltier element, the semiconductors and semiconductor junction parts included in the Peltier element are deteriorated, which may lead to the deterioration of the heating/cooling performance of the Peltier element. Along with this deterioration of the heating/cooling performance, there arises a problem in that the reliability of the temperature adjustment apparatus is lowered because it takes time for a target temperature to be reached, or it is difficult to accurately keep the target temperature.

For example, if a temperature adjustment apparatus is applied to a genetic test apparatus, and heating and cooling the temperature of a reaction liquid including a test substance and a reagent are repeated with the use of the polymerase chain reaction (PCR) method which is one of nucleic acid amplification technologies, it becomes possible to selectively amplify intended base sequences. Because such a temperature adjustment apparatus that performs a nucleic acid analysis technique typified by the PCR method repeatedly controls the temperature of a reaction liquid so that the temperature of the reaction liquid becomes various degrees C. such as 45° C., 65° C., or 95° C., it is necessary to repeat heating and cooling using Peltier elements in a short time. However, if the temperature control is performed in such a way in a state where the Peltier elements are deteriorated, the accuracy and speed of the temperature adjustment are lowered, so that an intended test cannot be achieved.

Therefore, a technique, in which whether a Peltier element has desired temperature adjustment performance or not is evaluated, and the intended test is prevented from stopping owing to the fact that the Peltier element has temperature performance lower than the desired temperature adjustment performance, is requested.

To meet this request, Patent Literature 1 discloses a technique in which the electric resistance of a Peltier element is calculated by measuring the current value and voltage value of the Peltier element, and the performance deterioration of the Peltier element is diagnosed from the change of the electric resistance.

Patent Literature 2 discloses a technique in which the change amount of temperature that is changed by a Peltier element per unit time is detected, and if the duty ratio of an input signal at the time of the detection is larger than a predefined value, the Peltier element is judged to be in a failed state.

CITATION LIST

Patent Literature

Patent Literature 1: Japanese Unexamined Patent Application Publication No. 2010-104382
Patent Literature 2: Japanese Unexamined Patent Application Publication No. 2008-232503

SUMMARY OF INVENTION

Technical Problem

In the diagnosis method disclosed in Patent Literature 1, the electric resistance of a Peltier element is calculated, and the change from the initial value of the electric resistance is used for diagnosing the performance deterioration of the Peltier element. In this case, the electric resistance of a Peltier element changes depending on the temperature of the Peltier element, and the temperature of the Peltier element keeps changing while heating/cooling cycles are repeated, so that the value of the electric resistance does not keep constant, and it is difficult to evaluate the degradation of the Peltier element very accurately. Furthermore, it is necessary to add measurement devices such as a current meter and a voltage meter to a temperature control apparatus, so that there arises a problem in that the configuration of the temperature control apparatus becomes complex.

In the case of the diagnosis method disclosed in Patent Literature 2, the deterioration of a Peltier element is judged using the change of the temperature of the Peltier element and whether or not the duty ratio of an input signal is larger than a threshold, therefore it is unnecessary to add a new measurement device. However, the change amount of the temperature caused by the Peltier element changes depending on the temperature of the Peltier element. In other words, the change amount of the temperature per unit time changes depending on the operation temperature of the Peltier element even if the duty ratio of the input signal is the same, therefore it is difficult to quantitatively evaluate the deterioration of the temperature adjustment performance of the Peltier element. In addition, there is a problem in that, because whether a Peltier element is abnormal or not is diagnosed using a threshold, there is no telling when the Peltier element is diagnosed as being abnormal.

The present invention has been achieved with the above-mentioned problems in mind, and relates to a temperature adjustment apparatus which uses a temperature adjustment element, and one of the objects of the present invention is to provide a highly reliable temperature adjustment apparatus capable of displaying a time at which the temperature adjustment performance of the temperature adjustment element is predicted to be below desired temperature adjustment performance or a warning based on the prediction result by making use of temperature data obtained from a temperature detection element.

Solution to Problem

A temperature adjustment apparatus, which is proposed by the present invention, includes: a temperature adjustment element; at least one temperature detection element provided near the temperature adjustment element; a calculation unit that calculates the output of the temperature detection element; and a display unit that displays at least one of a time calculated by the calculation unit as a time at which the temperature adjustment performance of the temperature adjustment element is predicted to be below desired temperature adjustment performance, the number of operations, and the time of current conduction, or a warning based on the result of calculation. Furthermore, the calculation unit includes: a prediction unit that calculates the predicted temperature of the temperature detection element; an input unit into which an actually measured temperature is input from the temperature detection element; and a comparison unit that compares the predicted temperature with the actually measured temperature, and calibrates the prediction unit so that the value of the predicted temperature and the value of the actually measured temperature coincide with each other; and the temperature adjustment apparatus calculates the temperature adjustment performance of the temperature adjustment element using a value obtained from the calibrated prediction unit.

Advantageous Effects of Invention

According to the present invention, a time at which the temperature adjustment performance of a temperature adjustment element is predicted to be below desired temperature adjustment performance or a warning based on the time at which the temperature adjustment performance is predicted to be below the desired temperature adjustment performance can be displayed by making use of temperature data obtained from a temperature detection element.

Problems, configurations, and advantageous effects other than the abovementioned items will become clear along with explanations regarding the following embodiments.

DESCRIPTION OF EMBODIMENTS

Hereinafter, the embodiments of the present invention will be explained with reference to the accompanying drawings.

First Embodiment

Figure 1:
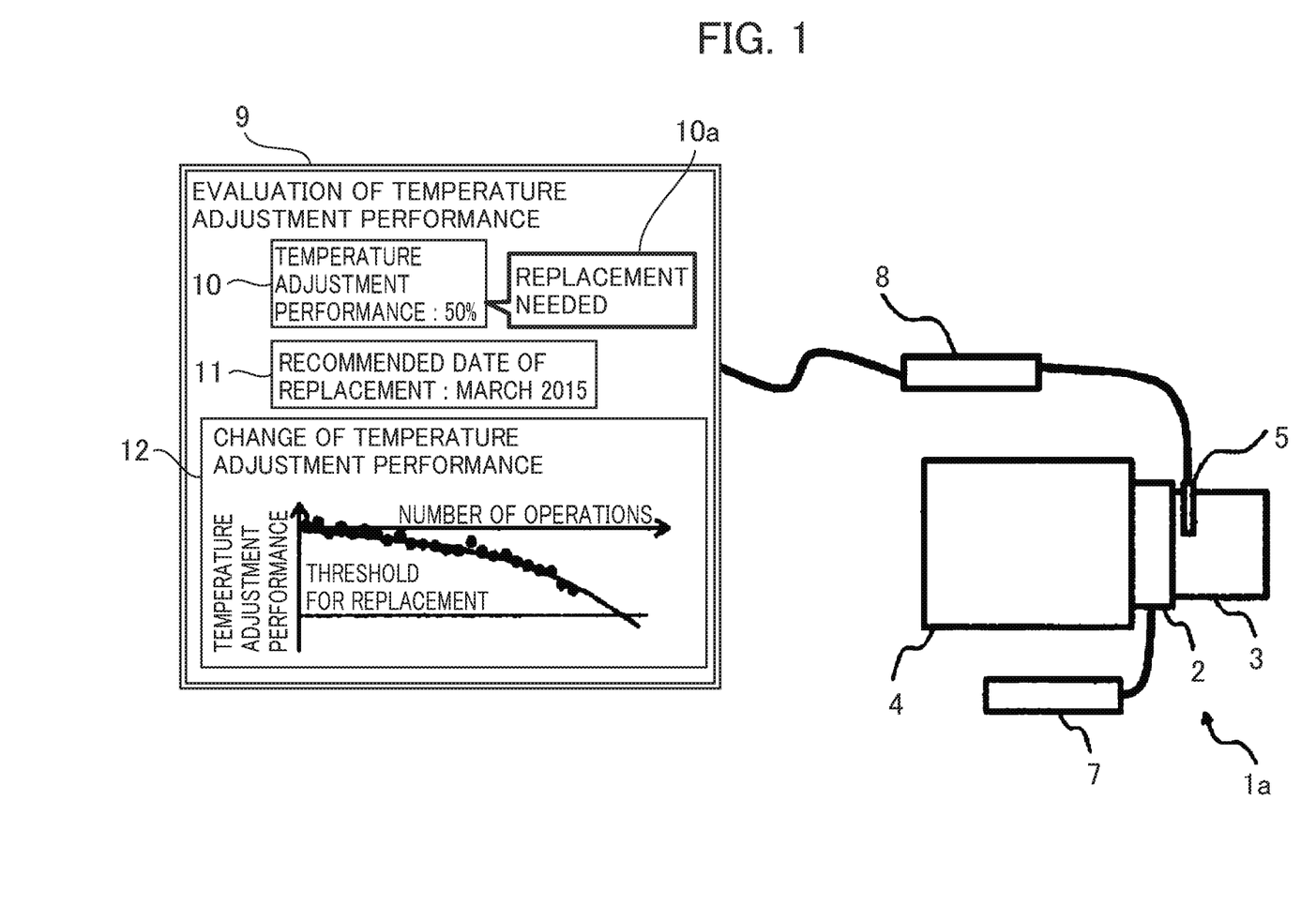
FIG. 1 is an overview entire block diagram schematically showing the entire configuration of a temperature adjustment apparatus according to a first embodiment of the present invention.

Hereinafter, a first embodiment of a temperature adjustment apparatus according to the present invention will be explained with reference to the accompanying drawings. FIG. 1 is an overview entire block diagram schematically showing the entire configuration of the temperature adjustment apparatus according to the first embodiment of the present invention.

The temperature adjustment apparatus 1 according to this embodiment mainly includes a temperature adjustment unit 1a, a calculation unit 8, and a display unit 9. The temperature adjustment unit 1a includes a temperature adjustment block 3 which is a target of temperature adjustment, a temperature detection element 5 for detecting the temperature of the temperature adjustment block 3, a temperature adjustment element 2 for adjusting the temperature of the temperature adjustment block 3, a securing block 4 for holding the temperature adjustment element 2, and a conduction current input unit 7 for inputting a conduction current output into the temperature adjustment element 2. The calculation unit 8 calculates the condition of the temperature adjustment performance of the temperature adjustment element 2 using a result obtained from the temperature detection element 5. The display unit 9 displays a predicted result of the calculation unit 8. Subsequently, the temperature of the temperature adjustment block 3 is adjusted so as to be equal to a predefined temperature by adjusting a conduction current output which is input into the temperature adjustment element 2 of the conduction current input unit 7 on the basis of a temperature that is input into a temperature control unit (not shown) after the temperature is detected by the temperature detection element 5 and input into the temperature control unit.

Figure 2:
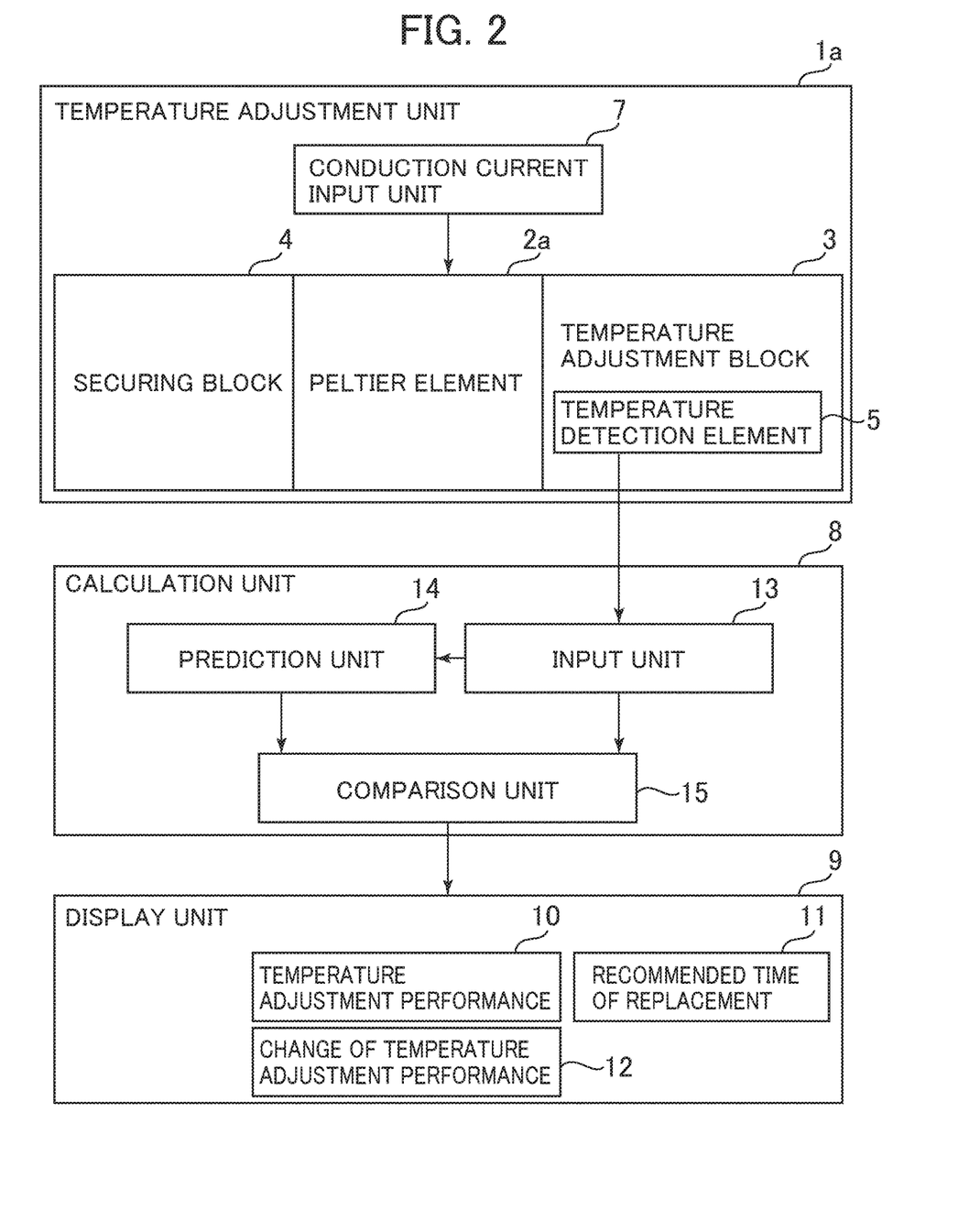
FIG. 2 is an explanatory diagram showing the functional blocks of the temperature adjustment apparatus according to the first embodiment of the present invention.

Here, as the temperature adjustment element 2, a Peltier element can be used, for example. The configuration of the functions of the temperature adjustment apparatus will be explained below with reference to FIG. 2. Here, although a Peltier element 2a is used as the temperature adjustment element 2 in FIG. 2, any element other than a Peltier element can be used as long as the element can be used as a temperature adjustable element. The Peltier element 2a shown in FIG. 2 is electrically connected to the conduction current input unit 7, and the Peltier element 2a heats up or cools down the adjacent temperature adjustment block 3 in accordance with the conduction current output from the conduction current input unit 7. In this case, heat generated from the opposite surface of the Peltier element 2a is radiated to the securing block 4.

Here, by making the securing block 4 out of material with high thermal conductivity such as aluminum or copper, heat generated at the securing block 4-side surface of the Peltier element 2a can be swiftly and efficiently diffused toward the securing block 4, therefore the temperature of the Peltier element can be kept uniform. In addition, by heating up the temperature of the securing block 4 using a temperature control device (not shown) such as a ceramic heater or a film heater, the temperature of the securing block 4 can be adjusted. With this, the securing block is cooled down, and the temperature of the securing block can be kept uniform. Furthermore, by cooling down the securing block 4 using a Peltier element, a cooling fan, or cooling water chiller unit, the temperature can be adjusted.

The display unit 9 displays the evaluation result of the temperature adjustment performance of the temperature adjustment element 2 calculated by the calculation unit 8. The display unit 9 displays, for example, the temperature adjustment performance 10, the recommended date of replacement 11, and the change of the temperature adjustment performance 12 of the temperature adjustment element 2. As for the display of the temperature adjustment performance 10, it is conceivable that the temperature adjustment performance 10 is represented not only by a numeric value but also, after the performance is classified in any arbitrary ranges, it is represented by any warning display 10a of, for example, three warning stage displays such as "good", "caution needed", and "replacement needed" in accordance with the current condition of the temperature adjustment performance. With this, a user of the apparatus can easily grasp the condition of the temperature adjustment performance, and by displaying any of the three warning stage displays without suddenly notifying the user of the abnormal condition of the temperature adjustment function, the user can easily prepare replacement and the like. In addition, the change of the temperature adjustment performance 12 can be displayed on the display unit 9 as a graph represented in a coordinate system having its vertical axis representing temperature adjustment performance and its horizontal axis representing time or the number of operations. With the use of this graph, the user can check how the performance of the temperature adjustment element has been deteriorating. Furthermore, it is also conceivable that the calculation unit 8 predicts the deterioration of the temperature adjustment performance in the future by approximating the relationship between the temperature adjustment performance and the time of operations or the number of operations of the temperature adjustment apparatus 1 with a polynomial expression, calculates the recommended date of replacement of the temperature adjustment element 2, and displays the recommended date of replacement 11. It is not always necessary to display the recommended date of replacement by a date in a year-month-day format, and a running time or the number of operations that remains until the performance reaches to a certain threshold used for recommending the replacement can be displayed instead.

The calculation unit 8 further includes an input unit 13 that brings in temperature data obtained from the temperature detection element 5, a prediction unit 14 that calculates the predicted temperature of the temperature detection element 5, and a comparison unit 15 that compares the temperature data input into the input unit 13 and the predicted temperature calculated by the prediction unit 14 with each other. Here, the predicted temperature of the temperature detection element 5 calculated by the prediction unit 14 can be calculated by calculation using a calculation expression, or by using a low-order simulation model such as a thermal fluid analysis model using which a thermal fluid simulation can be executed or a thermal network.

Next, calculation steps for evaluating the temperature adjustment performance of the temperature adjustment element 2 executed in the comparison unit 15 will be explained. The temperature adjustment apparatus 1 according to this embodiment evaluates the temperature adjustment performance of the temperature adjustment element by comparing temperature data regarding two points of the heat absorbing surface and the heat radiating surface of the temperature adjustment element 2 with the predicted temperature. In FIG. 2, by comparing temperature data detected by the temperature detection element 5 at the side of the temperature adjustment block 3 that is changed by the temperature adjustment element 2, temperature data detected at the side of the securing block 4, and the predicted temperature calculated by the prediction unit 14 with each other using the comparison unit 15, the temperature adjustment performance of the Peltier element 2 is evaluated.

In addition, an example, in which a data assimilation technique is used as a technique using which temperature data and predicted temperature are compared with each other and the temperature adjustment performance is evaluated in the comparison unit 15, will be explained. Data assimilation is a technique in which parameters regarding a simulation are corrected by comparing the simulation with a measured result, so that the accuracy of the simulation is improved.

Figure 3:
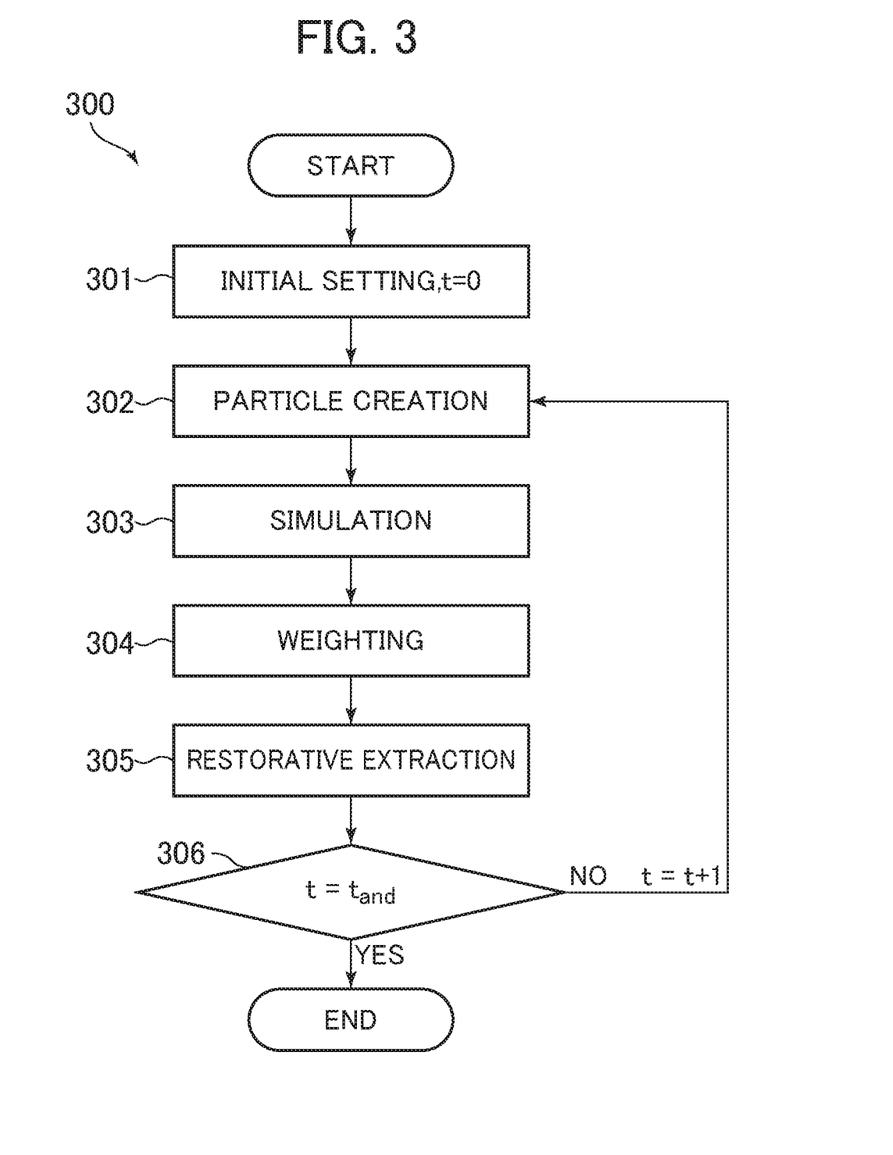
FIG. 3 is an explanatory diagram showing the calculation steps of data assimilation calculation executed by a comparison unit.

The calculation steps of data assimilation calculation 300 executed by the comparison unit 15 will be explained with reference to FIG. 3. First, in order to execute a simulation, the initial values of parameters such as temperature, a heat generation amount, and the like are set (Step 301).

Next, errors are given to the initial values of parameters which are set at Step 301 respectively. Here, a combination of a parameter and the corresponding error, which is used for executing the simulation, is referred to as a particle, and N particles with variation due to error for a parameter initial value are created (wherein N represents the number of the particles) (Step 302).

A simulation is performed regarding each of N particles (Step 303).

Here, it will be assumed that a combination of parameters that are used for a simulation at a certain time t represents a vector $x_t$. Furthermore, values that are actually observed such as temperature data are referred to as observed values, and it will be assumed that the observed values represents a vector $y_t$. Here, it will be assumed that a matrix that converts the vector $x_t$ including the parameters into the observed value $y_t$ is represented by $H_t$, and an error between the observed value $y_t$ and $H_t x_t$, which represents the result of the simulation, are represented by $w_t$, then the relationship among these values are given by Expression 1.

$$y_t = H_t x_t + w_t \qquad \text{[Expression 1]}$$

Next, N results calculated by the simulation and the observed results are compared with each other, and each particle is given a weight that shows how each particle approximates the corresponding observed result (Step 304). Calculations executed at this step are given by Expression 2 and Expression 3.

$$\lambda_t^{(i)} = p(y_t | x_{t|t-1}^{(i)}) \qquad \text{[Expression 2]}$$

$$\beta_t(i) = \lambda_t^{(i)} / (\Sigma_{j=1}^N \lambda_t^{(j)}) \qquad \text{Expression 3}$$

Here, p is a conditional probability. To put it concretely, p is a probability of $y_t$ occurring under the condition that $x_t$ is fixed, and $\lambda_t$ that is the result of the calculation is referred to as a likelihood, which is a value showing how $x_t$ approximates the observed value $y_t$. Each of subscripts "i" and "j" represents any of particle numbers "1" to "N". In addition, $\beta_t$ is a value given by normalizing the likelihood $\lambda_t$, and represents a weight given to the corresponding particle.

After the particles are given the corresponding weights respectively, restorative extraction is performed on each particle in accordance with a weight ratio corresponding to each particle (Step 305). With this operation, the ratio of particles having parameters using which calculated results nearer to the corresponding observed results are obtained is increased.

If the total simulation time has not elapsed yet, the flow goes back to Step 102, and the abovementioned calculations are repeated (Step 306).

By repeating these calculation steps, the parameter $x_t$ sets in the simulation are corrected so that the parameter $x_t$ makes the observed value $y_t$ reproduced more correctly, therefore this parameter $x_t$ transforms itself into a thermal analysis model that reproduces the observed value $y_t$ highly accurately.

Next, calculation steps for evaluating the temperature adjustment performance of the Peltier element 2a in the case where the above-described data assimilation calculation 100 is used in the comparison unit 15. The temperature data of the temperature detection element 5 input into the input unit 13 is transmitted to the comparison unit 15, and the data assimilation calculation 100 is performed on the temperature data. In the comparison unit 15, the thermal analysis model of the prediction unit 14 is corrected by the data assimilation calculation 100. The comparison unit 15 calculates the temperature adjustment performance and the recommended date of replacement of the Peltier element 2a using the corrected values, and transmits them to the display unit 9. The temperature adjustment performance 10 and the recommended date of replacement 11 are displayed on the display unit 9. However, it is conceivable that the comparison unit 15 performs calculation using not only the temperature data but also using the conduction current output data input from the conduction current input unit 7 into the Peltier element 2a.

Figure 4:
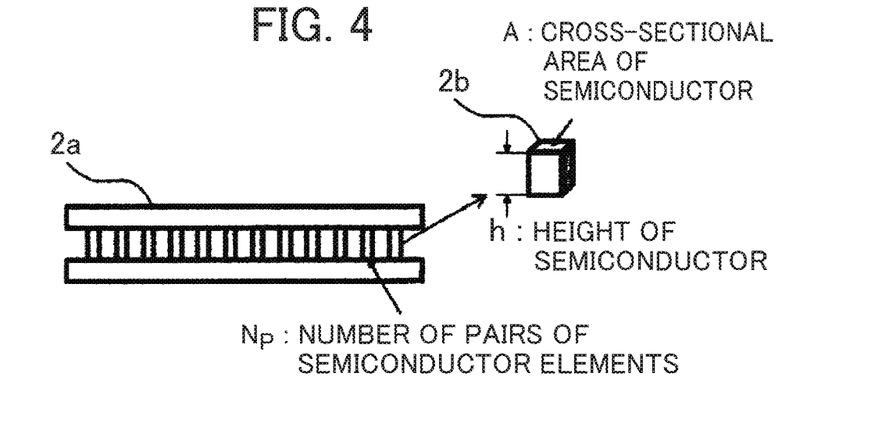
FIG. 4 is an overall structural diagram schematically showing the structure of a Peltier element according to the first embodiment of the present invention.

As for the evaluation of the temperature adjustment performance, for example, the temperature characteristic coefficients of the electric resistance of the Peltier element 2a that is dependent on the temperature of the Peltier element 2a can be used as indexes of the temperature adjustment performance. If the electric resistance of the Peltier element 2a increases, Joule heat increases at the time that the conduction current output is given to the Peltier element 2a, and heat absorbing amount or heat radiating amount of the Peltier element 2a changes, so that it becomes impossible to obtain desired temperature adjustment performance. Therefore, the temperature adjustment performance of the Peltier element can be evaluated with reference to the change of the electric resistance. Here, because the value of the electric resistance is dependent on the temperature, it is desirable that the electric resistance should be evaluated using temperature characteristic coefficients from which the effect of the temperature is removed. However, indexes used for calculating the temperature adjustment performance are not limited to the temperature characteristic coefficients, and temperature data or a conduction current output into the Peltier element 2a can also be used. Hereinafter, a calculation example in which the temperature characteristic coefficients of the resister of the Peltier element 2a are used as the indexes of the temperature adjustment performance will be explained. FIG. 4 shows an overall structural diagram of the Peltier element 2a. Furthermore, the relationship of the electric resistance of the Peltier element 2a and the temperature characteristic coefficients is given by Expression 4.

$$r = 2\frac{N_p h}{A}[\rho_0 + \rho_1 T + \rho_2 T^2] \quad \text{[Expression 4]}$$

In the above Expression, $N_p$ is the number of pairs of semiconductor elements included in a Peltier elements 2a, A represents the cross-sectional area of a semiconductor element, and h represents the height of the semiconductor element. In addition, $\rho_0$ represents a zeroth-order temperature characteristic coefficient, $\rho_1$ represents a first-order temperature characteristic coefficient, and $\rho_2$ represents a second-order temperature characteristic coefficient. Furthermore, T represents the temperature of the temperature detection element 5. The relations between these temperature characteristics and the temperature adjustment unit 1a are reproduced by the calculation unit 13 as calculation expressions. The value of $\rho_0$, the value of $\rho_1$, or the value of $\rho_2$ is calculated by the data assimilation calculation 100 that uses the obtained temperature data T. In this case, each of $\rho_0$, $\rho_1$, and $\rho_2$ is a coefficient independent of the temperature of the Peltier element 2a, so that the change of the temperature adjustment performance of the Peltier element 2a can be accurately evaluated regardless of a temperature condition under which the Peltier element 2a is disposed.

Figure 5:
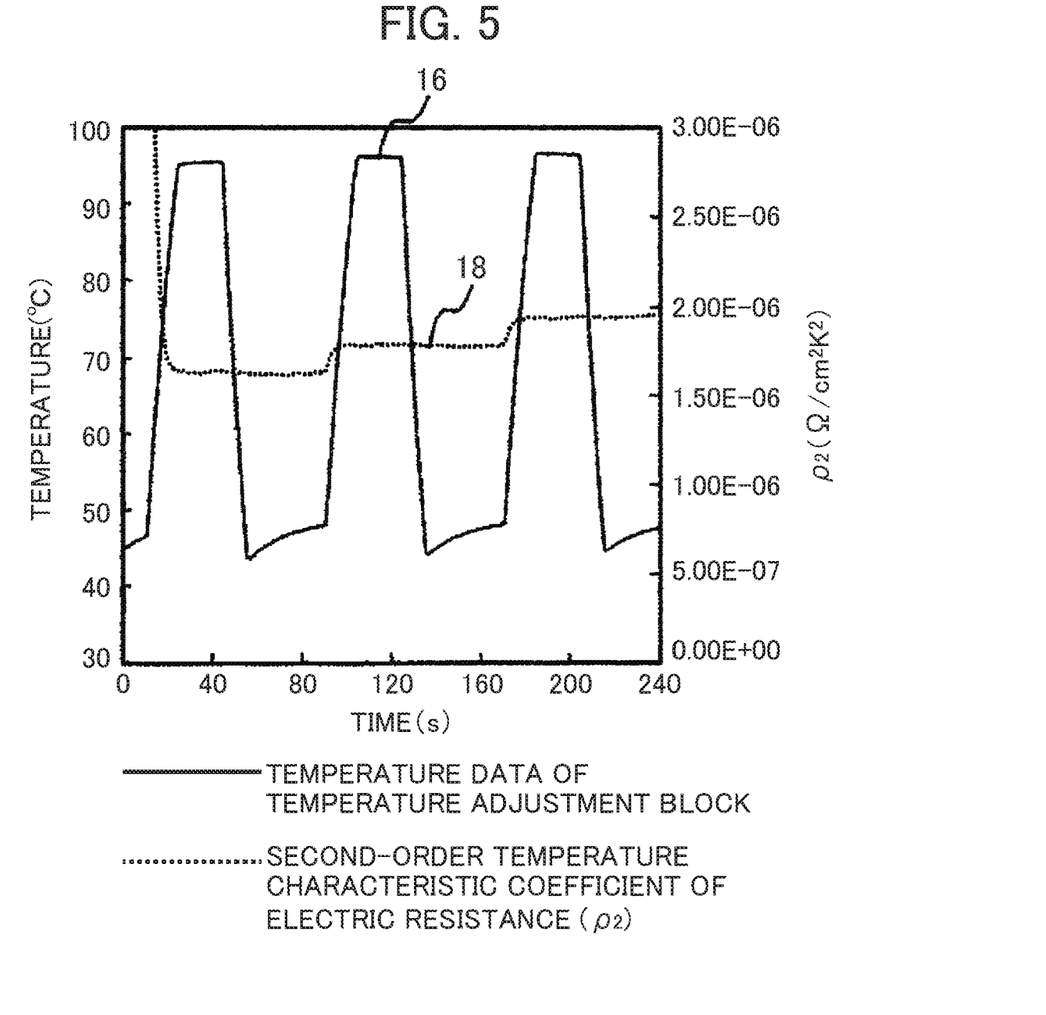
FIG. 5 is a diagram showing historical data regarding the prediction of the change of temperature and the temperature characteristic coefficients of an electric resistance executed by the temperature adjustment apparatus according to the first embodiment of the present invention.

FIG. 5 shows examples of temperature data 16 obtained from the temperature detection element 5 and the time variation 18 of $\rho_2$ obtained as a result of the data assimilation calculation 100. In FIG. 5, the value of $\rho_2$ is represented by the value of the right axis. By performing data assimilation calculation 100 on temperature measurement data obtained when the temperature adjustment block 3 is heated up or cooled down by the Peltier element 2a using the predicted temperature calculated by the prediction unit 14, $\rho_2$ is calculated, for example. After $\rho_2$ calculated by the comparison unit 15 is compared with the initial value of $\rho_2$ before the temperature cycle is executed on the Peltier element 2a, the difference between them is displayed on the display unit 9 as the change of the temperature adjustment performance.

For example, it is assumed that, when the temperature characteristic coefficient changes its value by 10% of its initial value, it is judged that the temperature adjustment performance goes down by 10%. For example, when the temperature adjustment performance goes down by 20%, we can judge that it is now the recommended date of replacement of the Peltier element 2a. Nevertheless, the threshold used for determining the recommended date of replacement can arbitrarily be decided by the management definition of the temperature adjustment apparatus 1.

Furthermore, although the evaluation of the temperature adjustment performance can be executed simultaneously while the temperature adjustment of the temperature adjustment unit 1a is being executed, it is also conceivable that the evaluation of the temperature adjustment performance is executed using temperature data stored in the input unit 13 when the temperature adjustment of the temperature adjustment unit 1a is not executed after the apparatus is activated, for example, once or a certain number of times a day. Alternatively, it is conceivable that an operator in charge of the temperature adjustment apparatus 1 evaluates the temperature adjustment performance at an arbitrary time as a maintenance work.

In addition, not only one temperature detection element 5 is always installed in the temperature adjustment apparatus 1a, but also plural temperature detection elements 5 can be installed, or one or more temperature detection elements 5 can be installed in the securing block 4, with the result that temperature measurement data increases, and the accuracy of the calculation of the temperature characteristic coefficients executed in the comparison unit 15 can be improved. Furthermore, not only the temperature data but also the conduction current output that is brought in by the Peltier element 2a can be used as a parameter used by the calculation unit 14, which leads the improvement of the accuracy of the calculation of the temperature characteristic coefficients.

Second Embodiment

Figure 6:
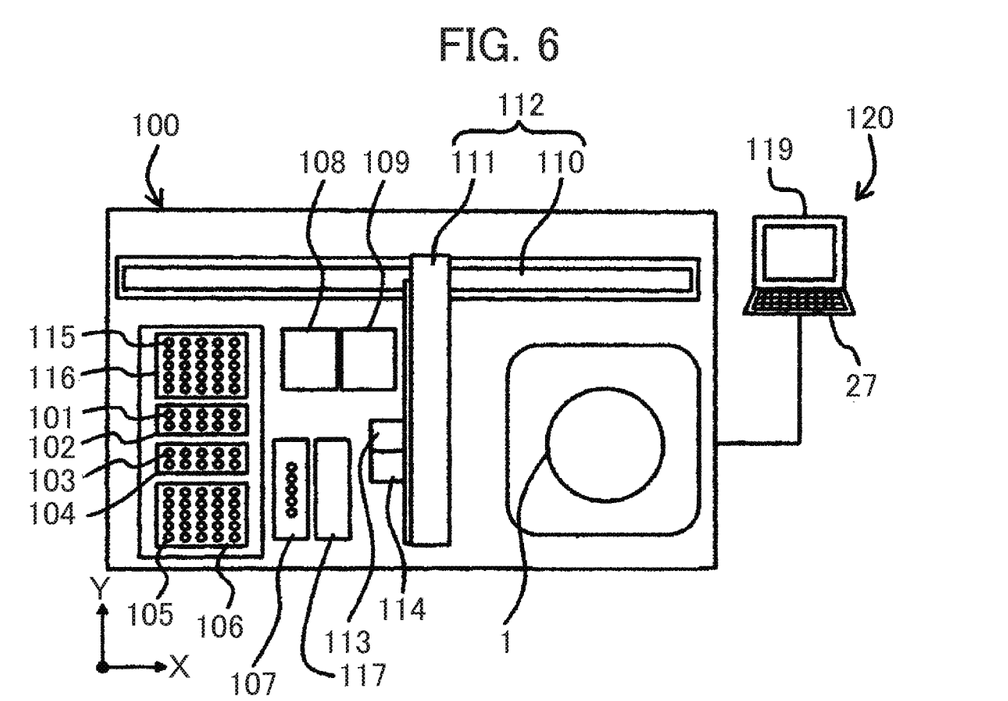
FIG. 6 is a schematic diagram showing the entire configuration of a nucleic acid test apparatus provided with a temperature adjustment apparatus according to a second embodiment of the present invention.

A second embodiment of the temperature adjustment apparatus 1 according to the present invention will be explained with reference to the accompanying drawings. This embodiment is shown in a diagram that schematically shows the entire configuration of a nucleic acid test apparatus 100 that includes plural temperature adjustment units 1a, and plural temperature adjustment blocks that can adjust temperature in synchronization with each other.

In the following explanation, the components of this embodiment that are the same as or similar to those of the above-described temperature adjustment apparatus are given the same reference signs in the relevant drawings, and detailed explanations about them will be omitted. As shown in FIG. 6, the nucleic acid test apparatus 100 includes plural sample vessels 101 each of which contains a test substance including a nucleic acid that is a target of amplification processing, a sample vessel rack 102 that houses the plural sample vessels 101, plural reagent vessels 103 that houses various reagents to be added to test substances, a reagent vessel rack 104 that houses the plural reagent vessels 103, reaction vessels 105 used for mixing the test substances with the reagents, a reaction vessel rack 106 that houses plural unused reaction vessels 105, a reaction liquid adjustment position 107 on which the unused reaction vessels 105 are mounted and that dispenses the test substances and the reagents from the sample vessels 101 and the reagent vessels 103 respectively to the relevant reaction vessels 105, a plugging unit 108 that seals the reaction vessels 105 each of which contains a reaction liquid, which is a mixed liquid including a test substance and a reagent, with lid members, and a stirring unit 109 that stirs the reaction liquids contained in the sealed reaction vessels 105.

In addition, the nucleic acid test apparatus 100 includes a robot arm device 112 having a robot arm X axis 110 that is installed on the nucleic acid test apparatus 100 so as to extend in the X axis direction (in the left-and-right direction in FIG. 6) and a robot arm Y axis 111 that is disposed so as to extend in the Y axis direction (in the up-and-down direction in FIG. 6) and that is installed movably in the X axis direction on the robot arm X axis 110, a gripper unit 113 that is installed movably in the Y axis direction on the robot arm Y axis 111 and that grips and conveys the reaction vessels 105 to the respective parts of the nucleic acid test apparatus 100, a dispensing unit 114 that is installed movably in the Y direction on the robot arm Y axis 111, sucks in test substances in sample vessels 101 and reagents in reagent vessels 103, and injects the test substances and the reagents into (dispenses the test substances and the reagents to) the reaction vessels 105 mounted on the reaction liquid adjustment position 107, nozzle chips 115 that are mounted on the parts of the dispensing unit 114 which are contactable with test substances and reagents, a nozzle chip rack 116 that houses plural unused nozzle chips 115, a nucleic acid amplification device 1 that performs nucleic acid amplification processing on the reaction liquids contained in the reaction vessels 105, a discarding box 117 in which used nozzle chips 115 and used (tested) reaction boxes 105 are discarded, and a control device 120 that includes input devices 118 such as a keyboard and a mouse, and a display device 119 such as a liquid crystal monitor, and controls the entire operation of the nucleic acid test apparatus 100 including the nucleic acid amplification device 1.

Figure 7:
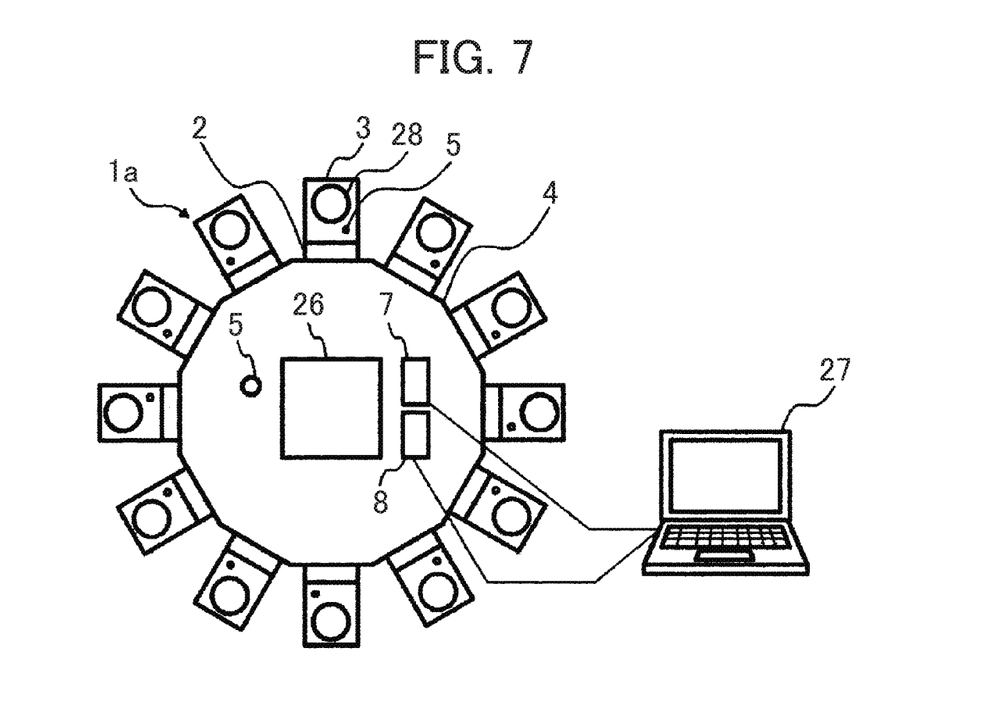
FIG. 7 is an overview entire block diagram schematically showing the entire configuration of the temperature adjustment apparatus according to the second embodiment of the present invention.
Figure 8:
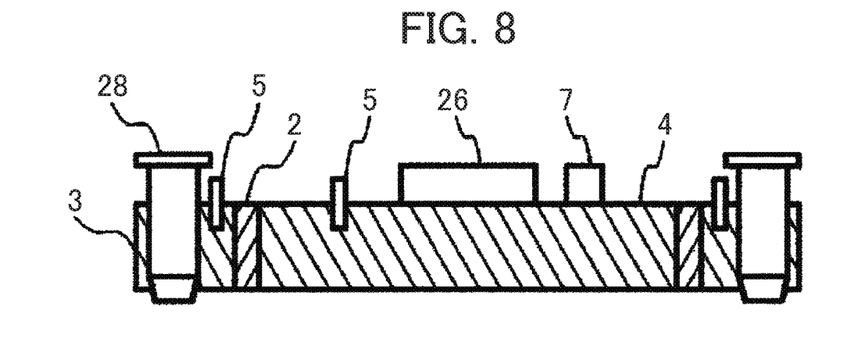
FIG. 8 is an overall cross-sectional view schematically showing a cross-sectional surface of the temperature adjustment apparatus according to the second embodiment of the present invention.

FIG. 7 is the overview entire block diagram of the temperature adjustment apparatus 1 shown in FIG. 6. In addition, FIG. 8 shows the overall cross-sectional view of the temperature adjustment apparatus 1 shown in FIG. 7. In the temperature adjustment apparatus 1 according to the present invention, not only one temperature adjustment unit 1a is always installed in a securing block 4, but also two or more temperature adjustment units can be installed on the side surface of the periphery portion of the securing block 4, for example. FIG. 6 shows an example in which a securing block 4 is formed, for example, in a dodecahedron body, and one temperature adjustment unit 1a is fixed on each side surface of the periphery portion of the securing block 4.

Furthermore, this embodiment shows an example in which the temperature adjustment apparatus is used as a temperature adjustment apparatus for reaction liquids in a PCR apparatus, and by fixing reaction vessels 28 including the reaction liquids to the temperature adjustment blocks 3 respectively, the temperature adjustment of the reaction liquids is executed. Here, a temperature adjustment block 3 holds not only one reaction vessel 28, but also two or more reaction vessels 28 can be fixed to the temperature adjustment block 3, and the temperature adjustment of the plural reaction vessels 28 can be executed at the same time. In addition, by installing a temperature detection element 5 and a temperature control device 26 in the securing block 4, the temperature of the securing block 4 is kept constant. Here, the temperature control device 26 can adjust the temperature 4 by heating up using a ceramic heater, a film heater, or the like, or can adjust the temperature by cooling down using a Peltier element, a cooling fan, a cooling water chiller unit.

Here, an input/output device 27 is connected to a conduction current input unit 7, and the temperature adjustment units 1a respectively performs temperature changing cycles different from each other. Therefore, the temperature adjustment performances of the temperature adjustment elements 2 are different from temperature adjustment unit 1a to temperature adjustment unit 1a depending on conditions under which the temperature adjustment elements 2 operate. Therefore, the control device 120 controls the arms lest the arms should put a reaction vessel in a temperature adjustment block 3 having a temperature adjustment element 2 the temperature adjustment performance of which is judged to be below desired temperature adjustment performance by a calculation unit. With this, it becomes possible that a reaction vessel is not put in a temperature adjustment block 3 which cannot perform a desired temperature adjustment, with the result that the quality of a PCR amplification result can be improved.

Here, one temperature detection element 5 is disposed in one temperature adjustment block 3 on a one-to-one basis. On the other hand, if the securing block 4 is made of material with high thermal conductivity such as aluminum or copper, the temperature distribution of the securing block 4 becomes small, so that it is conceivable that one temperature detection element 5 is installed in the securing block 4 and the temperature measured by this temperature detection element 5 is regarded as a representative temperature of the securing block 4. Nevertheless, not only one temperature detection element 5 is always installed in the securing block 4, and by disposing two or more temperature detection elements 5 in the securing block 4, the calculation accuracy of the data assimilation calculation 100 can be improved.

Figure 9:
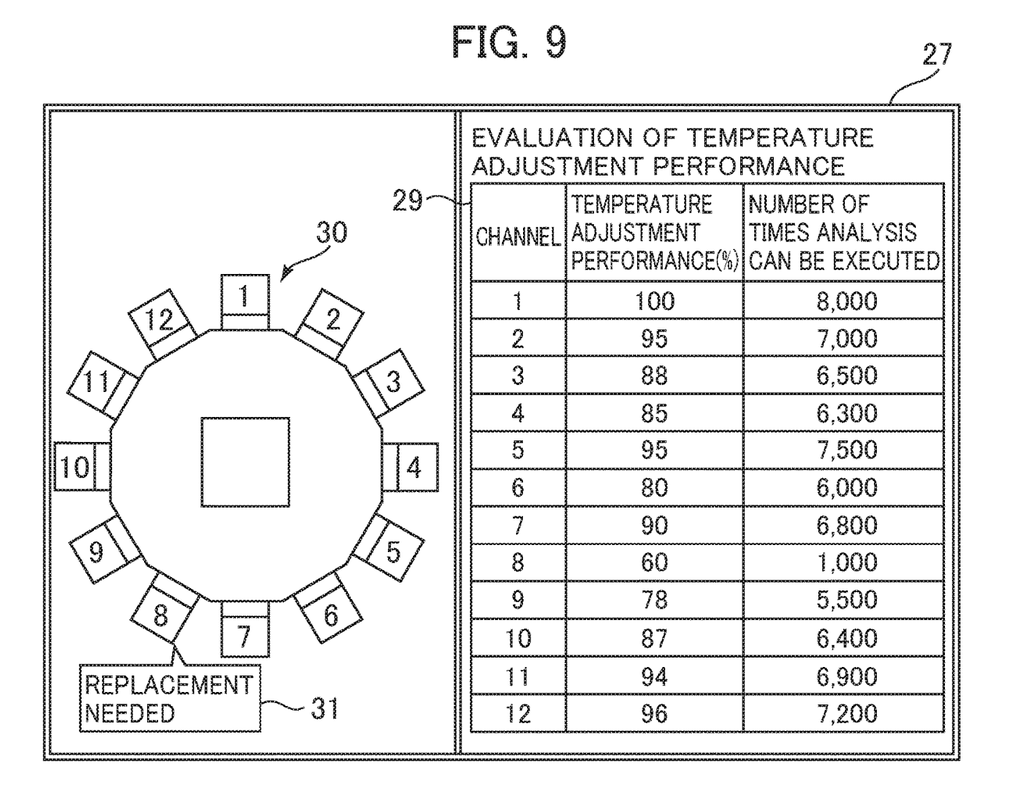
FIG. 9 is a diagram showing an example of a calculation result of a calculation unit displayed on the display screen of the input/output device of the temperature adjustment apparatus according to the second embodiment of the present invention.

FIG. 9 shows an example in which the input/output device 27 is also used as a display unit 9, and the temperature adjustment performance list display 29 of the temperature adjustment apparatus 1 and the positional information display 30 of the temperature adjustment apparatus 1 are shown on the display screen of the display unit 9. By displaying a temperature adjustment performance for each temperature adjustment unit 1a and the number of times the analysis can be executed by a PCR apparatus along with the positional information of the temperature adjustment apparatus 1 on the display screen, a temperature adjustment unit 1a the temperature adjustment performance of which is deteriorated can be clearly specified, so that, for example, by lowering the number of times of the operation repetitions of the temperature adjustment unit 1a the temperature adjustment performance of which is deteriorated, the deterioration of the temperature adjustment performance of the entirety of the temperature adjustment apparatus 1 can be uniformed, and the frequency of the maintenance execution of the temperature adjustment apparatus 1 can be reduced. In order to lowering the number of times of the operation repetitions of a temperature adjustment unit 1a the temperature adjustment performance of which is deteriorated, the control device 120 can control the arms lest the arms should put a reaction vessel in the temperature adjustment unit 1a the temperature adjustment performance of which is deteriorated. Nevertheless, the calculation result shown in the temperature adjustment performance list display 29 is not limited to the display of the number of times the analysis can be executed, and the recommended date of replacement or the number of times the operation can be executed can also be displayed. Furthermore, by displaying a time at which the temperature adjustment performance of a temperature adjustment element is predicted to be below desired temperature adjustment performance, the number of operations and the time of current conduction per temperature adjustment block having the temperature adjustment element 2, the maintenance efficiency can be more improved. In addition, as one of the numbers of operations, the number of PCR tests or the number of analyses that can be executed until the temperature adjustment performance is below the desired temperature adjustment performance can be displayed.

Furthermore, in the positional information display 30 of the temperature adjustment apparatus 1, by supplying a warning display 31 to a temperature adjustment unit 1a the temperature adjustment performance of which is deteriorated, the temperature adjustment unit 1a the temperature adjustment performance of which is deteriorated can be easily specified, which leads to the improvement of the maintenance efficiency.

LIST OF REFERENCE SIGNS

1: Temperature Adjustment Apparatus, 1a: Temperature Adjustment Unit,
2: Temperature Adjustment Element, 2a: Peltier Element, 2b: Semiconductor Forming Peltier Element,
3: Temperature Adjustment Block,
4: Securing Block,
5: Temperature Detection Element,
7: Conduction Current Input Unit,
8: Calculation Unit,
9: Display Unit,
10: Display of Temperature Adjustment Performance, 10a: Warning Display
11: Display of Recommended Date of Replacement
12: Display of Change of Temperature Adjustment Performance,
13: Input Unit,
14: Prediction Unit,
15: Comparison Unit,
16: Temperature Data of Temperature Adjustment Block,
18: Second-order Temperature Characteristic Coefficient of Electric Resistance,
26: Temperature Control Device,
27: Input/Output Device,
28: Reaction Vessel,
29: Temperature Adjustment Performance Evaluation List,
30: Display of Position of Temperature Adjustment Unit,
31: Warning Display,
300: Data Assimilation Calculation,
301: Initial Setting Step,
302: Particle Creation Step,
303: Simulation Step,
304: Weighting Step,
305: Restorative Extraction Step,
306: Analysis Time Diagnosis Step,
100: Nucleic Acid Test Apparatus,
101: Sample Vessel,
102: Sample Vessel Rack,
103: Reagent Vessel,
104: Reagent Vessel Rack,
105: Reaction Vessel,
106: Reaction Vessel Rack,
107: Reaction Liquid Adjustment Position,
108: Plugging Unit,
109: Stirring Unit,
110: Robot Arm X Axis,
111: Robot Arm Y Axis,
112: Robot Arm Device,
113: Gripper Unit,
114: Dispensing Unit,
115: Nozzle Chip,
116: Nozzle Chip Rack,
117: Discarding Box,
118: Input Device,
119: Display Device,
120: Control Device

The invention claimed is:

1. A temperature adjustment apparatus comprising:
a temperature adjustment element disposed adjacent to a temperature adjustment block and which raises and lowers a temperature of the temperature adjustment block based on a conduction current input received by said temperature adjustment element;
at least one temperature detection element provided near the temperature adjustment element; and
a display,
wherein the temperature adjustment element comprises a number, Np, of pairs of semiconductor elements,
wherein the temperature adjustment apparatus is configured to evaluate a change of temperature adjustment performance of the temperature adjustment element using change amounts of temperature characteristic coefficients of an electrical resistance, r, of the temperature adjustment element that are not dependent on temperature, said temperature adjustment apparatus being configured to determine said electrical resistance, r, based on said number Np of pairs of semiconductor elements of said temperature adjustment element, and wherein the display is configured to output at least one of a time at which the temperature adjustment performance of the temperature adjustment element is predicted to be below a desired temperature adjustment performance, a number of operations and a time of current conduction of the temperature adjustment element, or a warning.

2. The temperature adjustment apparatus according to claim 1, wherein the electrical resistance, r, is further determined based on a cross-sectional area of a semiconductor element A, a height of a semiconductor element h, temperature T, a zeroth-order temperature characteristic coefficient $\rho_0$, a first-order temperature characteristic coefficient $\rho_1$, and a second-order temperature characteristic coefficient by, according to $$r = 2\frac{N_p h}{A}[\rho_0 + \rho_1 T + \rho_2 T^2].$$

3. The temperature adjustment apparatus according to claim 2, wherein at least one value of $\rho_0$, $\rho_1$, and $\rho_2$ is a calculated value.

4. The temperature adjustment apparatus according to claim 3, wherein each of the values of $\rho_0$, $\rho_1$, and $\rho_2$ are calculated using a data assimilation technique.

5. The temperature adjustment apparatus according to claim 1, wherein the evaluation of the change of the temperature adjustment performance is determined by data assimilation in which simulation and a measurement result are compared with each other, and parameters regarding the simulation are corrected.

6. The temperature adjustment apparatus according to claim 1, wherein the number of operations is a number of tests or analyses which are conducted until a time at which the temperature adjustment performance of the temperature adjustment element becomes below the desired temperature adjustment performance.

* * * * *